US008026807B1

(12) United States Patent
Camhi

(10) Patent No.: US 8,026,807 B1
(45) Date of Patent: *Sep. 27, 2011

(54) MONITORING SYSTEM

(75) Inventor: Eli Camhi, Scarsdale, NY (US)

(73) Assignee: Accutrak Systems, Inc., Scarsdale, NY (US)

( * ) Notice: Subject to any disclaimer, the term of this patent is extended or adjusted under 35 U.S.C. 154(b) by 6 days.

This patent is subject to a terminal disclaimer.

(21) Appl. No.: 12/634,407

(22) Filed: Dec. 9, 2009

Related U.S. Application Data

(60) Continuation of application No. 12/125,215, filed on May 22, 2008, now Pat. No. 7,636,041, which is a continuation of application No. 11/317,606, filed on Dec. 23, 2005, now Pat. No. 7,378,961, which is a continuation-in-part of application No. 10/789,341, filed on Mar. 1, 2004, now Pat. No. 7,002,477, which is a division of application No. 09/294,034, filed on Apr. 19, 1999, now Pat. No. 6,762,684.

(51) Int. Cl.
*G08B 1/08* (2006.01)
*G05B 19/00* (2006.01)
*A61B 5/00* (2006.01)

(52) U.S. Cl. ............. 340/539.17; 340/5.52; 340/539.11; 340/539.12; 340/539.13; 340/573.1; 600/301; 128/903

(58) Field of Classification Search ............. 340/539.17, 340/5.52
See application file for complete search history.

(56) References Cited

U.S. PATENT DOCUMENTS

| | | | | |
|---|---|---|---|---|
| 6,762,684 | B1 * | 7/2004 | Camhi | 340/573.1 |
| 7,378,961 | B1 * | 5/2008 | Camhi | 340/539.17 |
| 7,636,041 | B1 * | 12/2009 | Camhi | 340/539.17 |

* cited by examiner

*Primary Examiner* — Donnie Crosland
(74) *Attorney, Agent, or Firm* — Seth Natter; Natter & Natter

(57) ABSTRACT

A monitoring system includes at least one fixed location monitoring station, a remote central station and a communications link interconnecting the monitoring station with the remote central station. The monitoring station includes a processor coupled to an input device for retrieving subject identification definition data and subject location definition data. The processor also retrieves physiological parameter sampling data from the subject and determines whether the physiological parameter sampling data lies within boundary limits of the identification definition data and also determines whether the location of the monitoring station lies within boundary limits of the location definition data. In the event the sampling data and the fixed location are within boundary limits, the processor may actuate an access control to permit the subject to enter or exit a controlled premises. Transaction logs including out of boundary conditions as well as in boundary conditions and the location of the monitoring station are transmitted to a remote central station.

12 Claims, 2 Drawing Sheets

MONITORING SYSTEM

RELATED APPLICATIONS

This application is a continuation of application Ser. No. 12/125,215 filed May 22, 2008, now U.S. Pat. No. 7,636,041 which is a continuation of application Ser. No. 11/317,606 filed Dec. 23, 2005, now U.S. Pat. No. 7,378,961 which is a continuation-in-part of application Ser. No. 10/789,341 filed Mar. 1, 2004, now U.S. Pat. No. 7,002,477, which is a division of application Ser. No. 09/294,034 filed Apr. 19, 1999, now U.S. Pat. No. 6,762,684, all of which are incorporated herein by reference in their entireties.

BACKGROUND OF THE INVENTION

1. Field of the Invention

The present invention relates to a system for monitoring a remote subject and more particularly to a system for identifying a monitored subject, ascertaining an out of boundary condition and transmitting event data pertaining to the monitoring activities to a central station.

2. Antecedent History

Various monitoring devices for promotion of safety and security of persons and property have been described in U.S. Pat. No. 5,825,283 entitled System for the Security and Auditing of Persons and Property, issued to Applicant herein on Oct. 20, 1998 and incorporated herein by reference.

While the previously known monitoring systems were capable of ascertaining the physical location of a subject as well as monitoring the status of vehicular functions and the like, e.g. U.S. Pat. No. 5,450,321, and were further capable of reducing the number of out of boundary condition reports by, for example, providing a time window within which an out of boundary condition may be corrected, as illustrated in U.S. Pat. No. 5,430,432 entitled Automotive Warning and Recording System, issued Jul. 4, 1995 to Applicant herein, there was a perceived need to provide a monitoring system with remote monitoring stations capable of monitoring an identifying physiological parameter associated with the subject, determining whether an out of boundary condition exists and conveying event data to a central station.

SUMMARY OF THE INVENTION

A processor implemented monitoring system includes one or more monitoring stations capable of monitoring an identifying physiological parameter of a subject such as a retinal scan, fingerprint scan, voice recognition, digital image, DNA characteristics, etc.

The monitoring station scans or otherwise receives subject definition data, i.e. an identifying physiological parameter and physical location boundary definition data relating to the identified subject, such as geographic areas where access is permitted or denied.

The monitoring station loads the definition data from a card or other device carried by the subject into a memory and then determines whether a physiological parameter sampling submitted by the subject is within boundary limits of the loaded physiological parameter data residing in the memory. If the physiological parameter is within boundary limits, the monitoring station processor then determines if the location of the monitoring station is within limits of the subject's location parameter data residing in the memory. If the monitoring station is associated with a controlled area entrance or exit portal, the processor then actuates an access to control to permit the monitored subject to enter or exit the controlled premises.

Each transaction is stored in an event log, with the event log data being transmitted to a central station via radio, cellular telephone, global communication network or other wired or wireless communications link. The event log data includes unique monitoring station identification data, such that the central station determines the specific geographic location of the occurrence reported.

The central station is also in communication with the monitoring station for loading or revising program software and optionally loading subject definition data.

The card or device carried by or attached to the subject may comprise a smart card, radio frequency transponder, inferred transmission device etc. for loading definition data, i.e. the subject physiological parameter data and the subject physical location boundary data into the monitoring station memory.

From the foregoing compendium, it will be appreciated that it is an aspect of the present invention to provide a monitoring system of the general character described which is not subject to the disadvantages of the antecedent history aforementioned.

It is a feature of the present invention to provide a monitoring system of the general character described which monitors a physiological parameter of a subject, ascertains the location of the subject and transfers event log information to a central station.

A consideration of the present invention is to provide a monitoring system of the general character described which monitors a unique identity parameter of a subject and ascertains whether the subject is seeking access to an authorized location.

Another aspect of the present invention to provide a monitoring system of the general character described which monitors a physiological parameter of a subject, ascertains whether the subject is at a permitted location and transfers event log information to a central station.

A still further feature of the present invention is to provide a monitoring system of the general character described which assures that only authorized personnel are within a monitored area.

To provide a monitoring system of the general character described which includes a processor implemented monitoring station capable of monitoring a number of subjects with relatively low memory requirements is yet another consideration of the present invention.

Yet another aspect of the present invention is to provide a monitoring system of the general character described which employs a plurality of monitoring stations to control access to premises having internal areas where access is permitted to only certain individuals among those who have been permitted access to the overall premises.

Other aspects, features and considerations of the present invention in part will be obvious and in part will be pointed out hereinafter.

With these ends in view, the invention finds embodiment in various combinations of elements, arrangements of parts and series of steps by which the above-mentioned aspects, features and considerations and certain other aspects, features and considerations are attained, or with reference to the accompanying drawings and the scope of which will be more particularly pointed out and indicated in the appended claims.

BRIEF DESCRIPTION OF THE DRAWINGS

In the accompanying drawings in which is shown one of the various possible exemplary embodiments of the invention.

DESCRIPTION OF THE PREFERRED EMBODIMENTS

Figure 1:
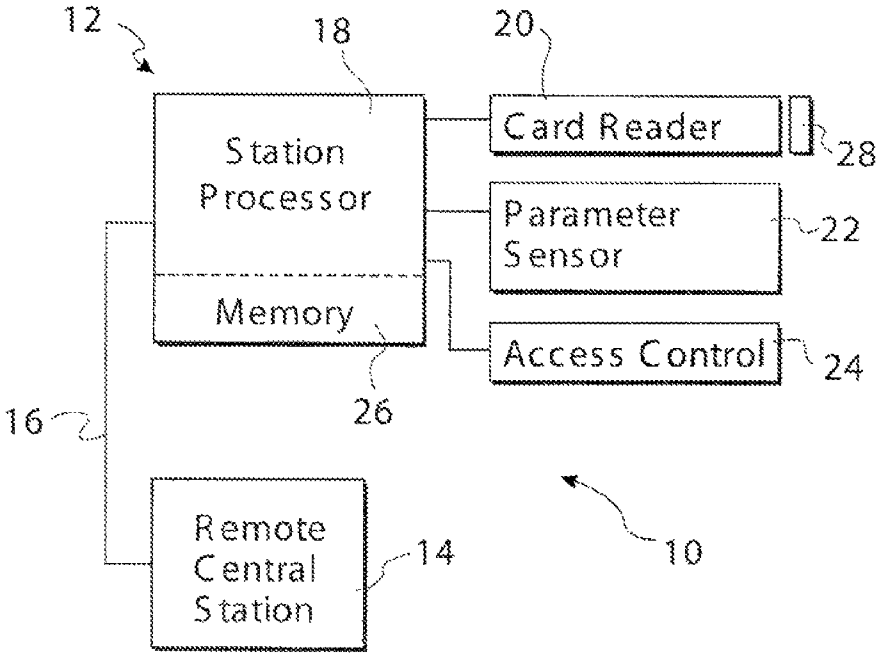
FIG. 1 is a schematized view of a monitoring system constructed in accordance with and embodying the invention depicted in simplified block format with a monitoring station comprising a station processor coupled to a card reader, a parameter sensor and an access control and also coupled to a remote central station by a communications link.

Referring now in detail to the drawings, the reference numeral 10 denotes generally a monitoring system constructed in accordance with and embodying the invention. The monitoring system 10 includes at lease one monitoring station 12 coupled to a remote central station 14 by a communications link 16.

The monitoring station 12 includes a station processor 18. The processor 18 is interconnected to an input device 20 which may comprise a card reader, to an input device 22, which may comprise a physiological parameter sensor and to a peripheral device 24, which may comprise an access control, such as a gate or door mechanism. There is also associated with the station processor 18 a memory 26 which stores data representative of the physical location of the monitoring station.

In accordance with one aspect of the invention, the memory 26 is not required to store subject definition data for all monitored subjects because the definition data pertaining to each monitored subject is carried with or affixed to the subject in a smart card 28 or other portable memory device such as a flash memory card, a radio tag or transponder or may be directly coupled to the processor through a suitable port, such as a USB port. Accordingly, the input device 20, should not be construed as solely a card reader but may encompass any other data input device capable of receiving subject definition data.

Figure 3:
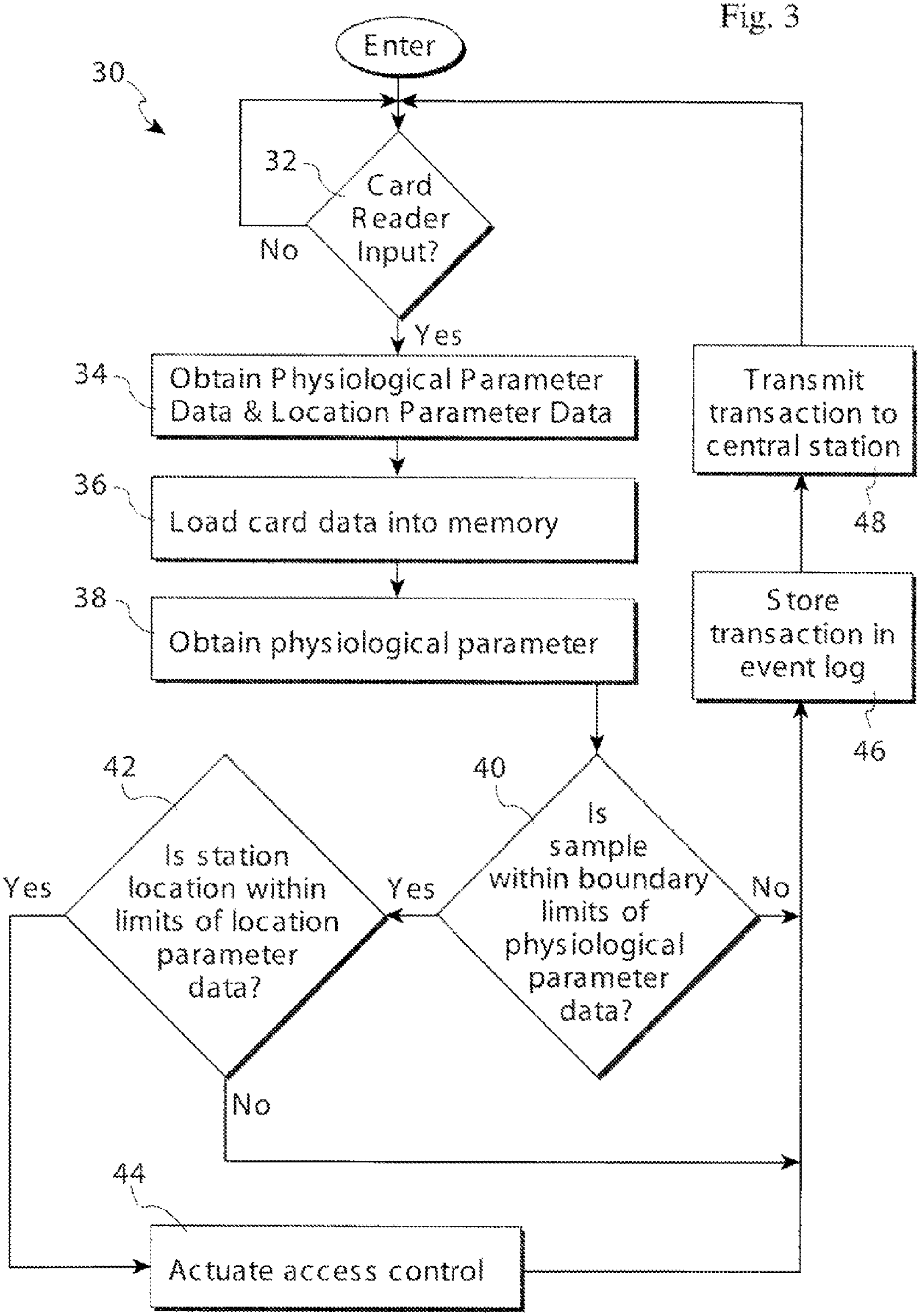
FIG. 3 is a schematized diagrammatic representation of a typical routine for a monitoring station processor pursuant to which a subject is identified and access to a controlled area is granted only after the subject's identity and authorization to access the controlled area have been verified.

The operation of the monitoring station 12 may be more readily appreciated from an examination of FIG. 3 wherein a typical processor routine 30 is depicted.

Upon entry into the routine 30, the processor 18 ascertains whether or not there is an input signal at the input device 20, as indicated in an inquiry box 32. If an input is present, the processor 18 obtains the subject definitions, i.e. physiological parameter data and location parameter data, as indicated in a block 34. Thereafter, the processor 18 loads the subject definition data into the memory 26 as indicated in a block 36. If the memory 26 has stored previous subject definition data, the processor 18 may overwrite such previous data to conserve memory requirements.

Thereafter, a subject physiological parameter sample is taken at the parameter sensor 22, as indicated in a block 38. It should be appreciated that the physiological parameter sensor 22 will input to the processor 18 unique subject identification data obtained as a result of a retinal scan, fingerprint scan, etc.

The processor 18 then ascertains whether or not the physiological parameter sample data obtained is within the boundary limits of the physiological parameter definition data residing in the memory 26, as indicated at a box 40. In the event the physiological sample data is not within the boundary limits, the processor stores the transaction in an event log as indicated at a block 46 and may immediately transmit the event log data to the remote central station 14, as indicated in a block 48, before returning.

Optionally, the processor 18 may permit a given number of physiological parameter samples to be submitted before storing the transaction in the event log and/or transmitting the event log data and returning to the inquiry box 32.

In the event the physiological parameter sample falls within the limits of the stored data, the processor 18 then proceeds to a further inquiry to determine whether the location of the monitoring station 12 is within the limits of the subject location parameter definition data. If the monitoring station location or the entrance or exit portal controlled by the monitoring station is not a permitted location for the subject, the processor stores the transaction in the event log, as indicated in the block 46 and returns to the inquiry box 32 or may immediately transmit the event log data to the remote central station 14, as indicated in the block 48 and then return to the inquiry box 32.

In the event the station location is a permitted location for the subject and the monitoring station is controlling an entrance or exit portal, the processor then actuates the access control 24 to permit the subject to pass beyond the entrance or exit portal, as indicated at a block 44. The processor 18 then stores the transaction in the event log, as indicated in the block 46 and may transmit the event log data to the remote central station, as indicated in the block 48 before returning to the inquiry box 32.

It should be appreciated that the transmission of the event log of each event to the remote central station may be immediate, upon the occurrence of each event or the processor may store event log transactions over a period of time and then transmit a group of transactions to the remote central station 14.

The advantage to immediately transmitting each event log occurrence is that personnel or processor implemented oversight systems at the remote central station will have a real time knowledge of monitoring station transactions and may take immediate action as deemed necessary in the event of irregular or inappropriate activities.

The central station 14 may forward all or selected event log occurrences to a distribution list of computers, e-mail address or the like. Well known encryption technologies may be employed for communications on the communications link 16 and from the central station 14 to entities on the distribution list.

Figure 2:
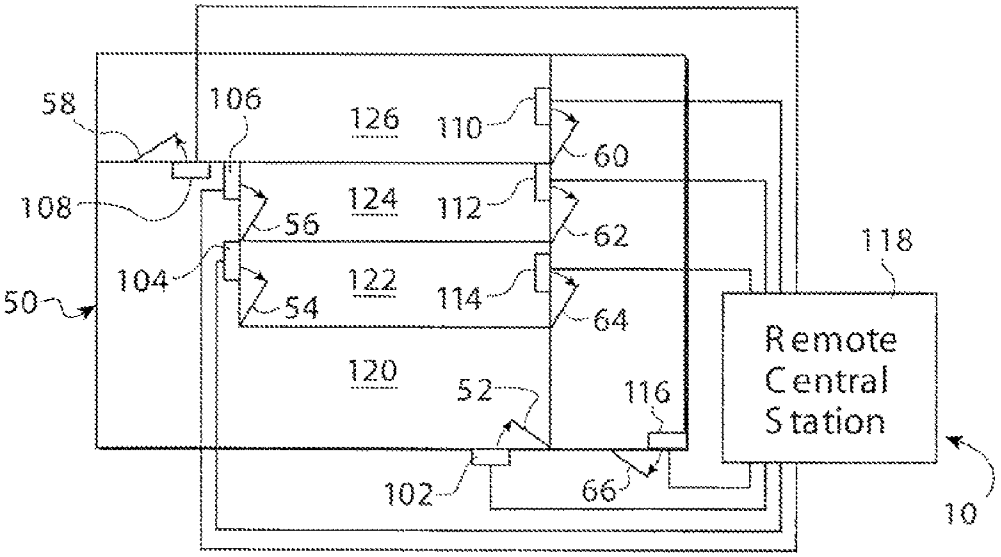
FIG. 2 is a reduced scale schematized illustration of the monitoring system at a controlled premises having a plurality of internal areas with access to the premises and each of the internal areas being controlled by a monitoring station and with a communications link interconnecting each monitoring station and a remote central station.

In FIG. 2 there is depicted a monitoring system wherein a plurality of monitoring stations are deployed throughout a controlled premises 50, which might comprise a building or portion thereof operated by a business dealing in sensitive information, a correctional institution or an apartment dwelling, for example.

The premises 50 includes a main entrance doorway 52, as well as a plurality of interior entrances 54, 56, and 58. The premises 50 may also include exit portals through interior spaces such as exit portals 60, 62, 64 and 66.

There is also provided a monitoring station 102 associated with the entrance 50, a monitoring station 104 associated with the interior entrance 54, a monitoring station 106 associated with the interior entrance 56 and a monitoring station 108 associated with the interior entrance 58.

Each exit portal may also have an associated monitoring station, for example, a monitoring station 110 associated with the exit portal 60, a monitoring station 112 associated with the exit portal 62, a monitoring station 114 associated with the exit portal 64 and a monitoring station 116 associated with the exit portal 66.

Each of the monitoring stations 102, 104, 106, 108, 110, 112, 114, and 116 is substantially identical to the monitoring station 12 previously described and depicted in FIG. 1 and include a linked input device or card reader, a linked parameter sensor and a linked access control coupled to the associated entrance or exit portal.

Additionally, as will be noted in FIG. 2, each of the monitoring stations is coupled by a communications link to a remote central station 118.

In operation, a subject would present his or her own definition data card 28 to be scanned or otherwise read by the input device 20 and thereafter submit an identifying physiological sample at the parameter sensor. The station processor then proceeds with the routine 30 and either permits or denies access through each of the successive entrances. Thus for example, in a secure establishment requiring clearance to enter various interior areas, the subject will gain access to a common interior room 120 and one or more successive interior rooms denoted by the reference numerals 122, 124 and 126, only as authorized by the subject's security clearance, i.e. location parameter definition data. Entry or denial of entry into each of the interior rooms is logged and a report is transmitted to the remote central station 118. Further, although a subject may exit an interior room through the entrance controller by a first monitoring station, in some instances, the subject exits through a separate exit portal controlled by a separate monitoring station and the transaction is entered in the appropriate transaction log.

In an environment such as a multiple dwelling structure, each subject's card 28 will permit access to a main lobby 120 and the subject's individual apartment 122, 124, for example, and also permit access to controlled semipublic areas such as a laundry room, gym, etc. 12 only if such access is authorized. A monitoring station may also be employed to gain access to specific equipment within the controlled premises such as, for example, gym equipment or laundry machines, or, computer terminals, etc. with the access control 24 coupled to an equipment switch.

It should also be noted that monitoring stations may be deployed in situations wherein access control is not required. For example, monitoring stations may be employed within or at peripheral locations of an area wherein a subject is confined, with the subject being required to submit a physiological parameter specimen at preset time intervals. If relatively few subjects are being monitored, the employment of a card 28 or the like for retrieval of the subject definition data may not be necessary, since the definition data of a limited number of subjects may be stored in the station processor memory 26. An aspect of the invention however, is the ability to utilize relatively little memory for monitoring a relatively large number of subjects, since the subject card 28 carries each subject's definition data which is loaded into the memory and thereafter overwritten.

A further aspect of the invention is the ability to utilize the input device 20 to retrieve limited or incomplete definition data. For example, the input device 20 may comprise a keypad or scanner which just retrieves subject identification data, e.g. a pin number, without the definition data. The processor 18 then requests complete definition data attributable to the subject having the pin number from the central station 14 and retrieves the definition data over the communications link 16.

Thus it will be seen that there is provided a monitoring system which achieves the various aspects, features and considerations of the present invention and which is well adapted to meet the conditions of practical usage.

Having thus described the invention, there is claimed as new and desired to be secured by Letters Patent:

1. A method of controlling access at a monitored location, the method comprising the steps of:

a) storing in a memory data representative of the monitored location, b) receiving physiological parameter identification definition data of a subject authorized to have access, c) receiving location definition data of the subject authorized to have access, d) obtaining physiological parameter sampling data from the subject, e) comparing the physiological parameter sampling data with the physiological parameter identification definition data, f) comparing the data representative of the monitored location with the subject location definition data, and g) granting access if the physiological parameter sampling data lies within boundary limits of the physiological parameter definition data and the data representative of the monitored location lies within the boundary limits of the subject location definition data.

2. A method of controlling access at a monitored location in accordance with claim 1 further including:

h) denying access if the physiological parameter sampling data does not lie within boundary limits of the physiological parameter definition data, or the data representative of the monitored location does not lie within boundary limits of the subject location definition data.

3. A method of controlling access at a monitored location in accordance with claim 1 further including:

h) generating a transaction event log if the physiological parameter sampling data does not lie within boundary limits of the physiological parameter definition data, i) generating a transaction event log if the data representative of the fixed location does not lie within boundary limits of the subject location definition data.

4. A method of controlling access at a monitored location in accordance with claim 3 further including:

j) denying access if the physiological parameter sampling data does not lie within boundary limits of the physiological parameter definition data, or the data representative of the monitored location does not lie within boundary limits of the subject location definition data.

5. A method of controlling access at a monitored location in accordance with claim 1 further including the steps of storing the subject physiological parameter identification data in the memory prior to performing step e) and storing the subject location definition data in the memory prior to performing step f).

6. A method of controlling access at a monitored location in accordance with claim 5 wherein the steps of storing are performed by writing over previously stored subject physiological parameter identification data and previously stored subject location definition data.

7. A method of controlling access at a monitored location in accordance with claim 1 wherein step b) is performed by accessing a portable memory device carried by the subject.

8. A method of controlling access at a monitored location in accordance with claim 7 wherein step c) is performed by accessing a portable memory device carried by the subject.

9. A method of controlling access at a monitored location in accordance with claim 1 wherein step c) is performed by accessing a portable memory device carried by the subject.

10. A method of controlling access at a monitored location in accordance with claim 1 wherein step b) is performed by accessing a remote central station.

11. A method of controlling access at a monitored location in accordance with claim 10 wherein step c) is performed by accessing a remote central station.

12. A method of controlling access at a monitored location in accordance with claim 1 wherein step c) is performed by accessing a remote central station.

* * * * *